US012324908B2

(12) United States Patent
Lin et al.

(10) Patent No.: US 12,324,908 B2
(45) Date of Patent: Jun. 10, 2025

(54) THERMOELECTRIC DRIVING WEARABLE SYSTEM

(71) Applicant: NATIONAL TSING HUA UNIVERSITY, Hsinchu (TW)

(72) Inventors: Zong-Hong Lin, Hsinchu (TW); Hua-Shan Wu, Hsinchu (TW); Hsuan-Yu Ho, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 278 days.

(21) Appl. No.: 18/167,080

(22) Filed: Feb. 10, 2023

(65) Prior Publication Data
US 2024/0165399 A1 May 23, 2024

(30) Foreign Application Priority Data
Nov. 23, 2022 (TW) ................................ 111144857

(51) Int. Cl.
*A61N 1/04* (2006.01)
*A61N 1/28* (2006.01)
*A61N 1/36* (2006.01)
*H10N 19/00* (2023.01)

(52) U.S. Cl.
CPC .......... *A61N 1/048* (2013.01); *A61N 1/0468* (2013.01); *A61N 1/0476* (2013.01); *A61N 1/28* (2013.01); *A61N 1/36034* (2017.08); *H10N 19/00* (2023.02)

(58) Field of Classification Search
None
See application file for complete search history.

(56) References Cited

U.S. PATENT DOCUMENTS

| 5,817,139 A * | 10/1998 | Kasano .................. A61N 1/326 607/72 |
| 10,905,876 B2 * | 2/2021 | Hsu ....................... A61N 1/0468 |
| 2007/0179585 A1 * | 8/2007 | Chandler ............... A61N 1/326 623/1.1 |
| 2009/0182392 A1 * | 7/2009 | Woolaston ......... A61N 1/36038 607/57 |
| 2016/0303293 A1 * | 10/2016 | Doyle ............... A61B 10/0233 |

(Continued)

FOREIGN PATENT DOCUMENTS

| CN | 102946797 A | 2/2013 |
| CN | 110279939 A | 9/2019 |

(Continued)

*Primary Examiner* — Michael W Kahelin
(74) *Attorney, Agent, or Firm* — CKC & Partners Co., LLC

(57) ABSTRACT

A thermoelectric driving wearable system includes a thermoelectric device and an electrical stimulating assembly. The thermoelectric device includes two thermal interface material layers and a thermoelectric converting layer. The two thermal interface material layers are configured for contacting a heat source and a cold source, respectively. The thermoelectric converting layer is located between the two thermal interface material layers and configured for generating an electric energy according to a temperature difference between the heat source and the cold source. The electrical stimulating assembly is electrically connected to the thermoelectric device and configured for being disposed at a skin surface, and the electrical stimulating assembly receives the electric energy and transmits a current to a stimulated region.

12 Claims, 19 Drawing Sheets

(56) References Cited

U.S. PATENT DOCUMENTS

| | | | | |
|---|---|---|---|---|
| 2017/0043154 | A1* | 2/2017 | Pelssers | A61N 1/325 |
| 2019/0134408 | A1* | 5/2019 | Von Novak, III | H02J 50/00 |
| 2022/0184406 | A1* | 6/2022 | Lycke | A61N 1/3904 |
| 2024/0350797 | A1* | 10/2024 | Jiang | A61N 1/0484 |

FOREIGN PATENT DOCUMENTS

| | | |
|---|---|---|
| CN | 111132726 A | 5/2020 |
| CN | 111699018 A | 9/2020 |
| CN | 113226448 A | 8/2021 |

\* cited by examiner

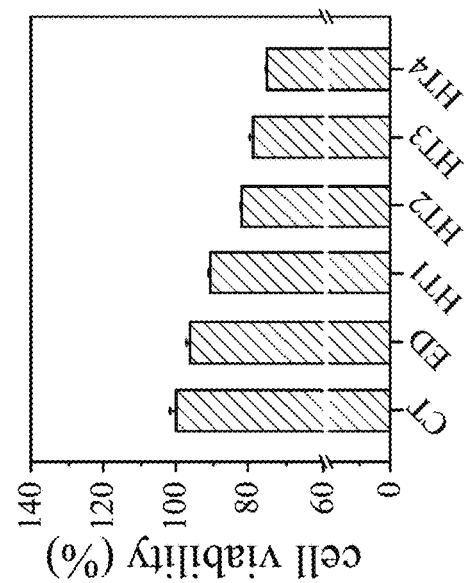
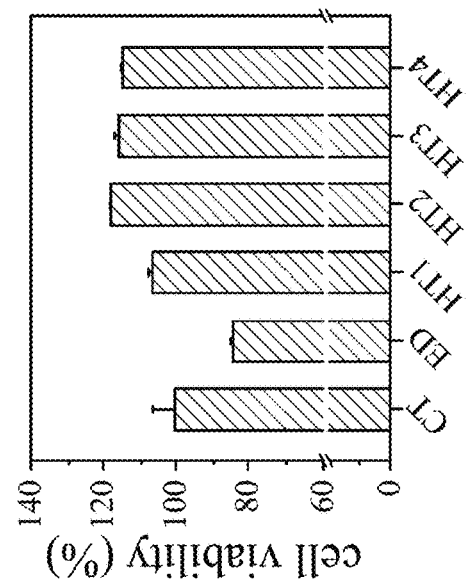
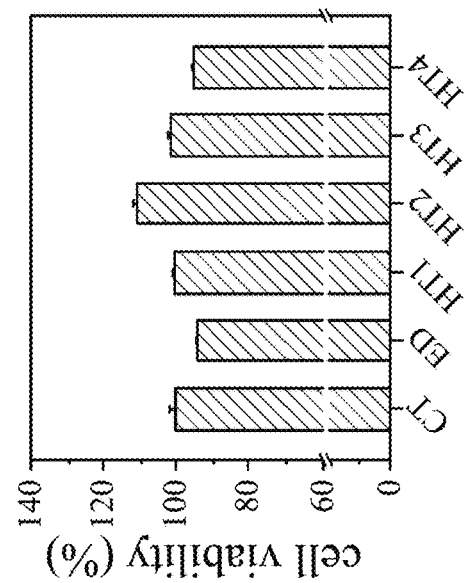
Fig. 12A
Fig. 12B
Fig. 12C

THERMOELECTRIC DRIVING WEARABLE SYSTEM

RELATED APPLICATIONS

This application claims priority to Taiwan Application Serial Number 111144857, filed Nov. 23, 2022, which is herein incorporated by reference.

BACKGROUND

Technical Field

The present disclosure relates to a wearable system. More particularly, the present disclosure relates to a thermoelectric driving wearable system disposed at a skin surface.

Description of Related Art

With the advance of the medical technologies, there are various of methods of curing the wound on a skin surface such as oxygen/hyperbaric equipment, negative pressure wound therapy system, etc., and the curing method of electrical stimulation (ES) has become a major technology because of the non-disposable design with lower cost. However, the conventional electrical stimulation method is to stimulate the wound by electrodes with an external power supply, so it needs to replace the battery regularly and cannot be worn easily. Moreover, the voltage of the electric energy is unstable due to the decreasing of the power supply, which may cause that the wound cannot be cured effectively, or even the wound can be injured more.

Accordingly, a self-powered and stable powering thermoelectric driving wearable system is still a goal which the practitioners pursue.

SUMMARY

According to one aspect of the present disclosure, a thermoelectric driving wearable system includes a thermoelectric device and an electrical stimulating assembly. The thermoelectric device includes two thermal interface material layers and a thermoelectric converting layer. The two thermal interface material layers are configured for contacting a heat source and a cold source, respectively. The thermoelectric converting layer is located between the two thermal interface material layers and configured for generating an electric energy according to a temperature difference between the heat source and the cold source. The electrical stimulating assembly is electrically connected to the thermoelectric device and configured for being disposed at a skin surface, and the electrical stimulating assembly receives the electric energy and transmits a current to a stimulated region.

BRIEF DESCRIPTION OF THE DRAWINGS

The present disclosure can be more fully understood by reading the following detailed description of the embodiment, with reference made to the accompanying drawings as follows:

FIG. 12A shows a measurement of cell viabilities of a thermoelectric driving wearable system according to a first treatment example of the present disclosure with the heat source at the different temperatures, a first controlled example and a first comparison example in the stimulating time as being 10 minutes.

FIG. 12B shows a measurement of the cell viabilities of the thermoelectric driving wearable system according to the first treatment example in FIG. 12A with the heat source at the different temperatures, the first controlled example and the first comparison example in the stimulating time as being 15 minutes.

FIG. 12C shows a measurement of the cell viabilities of the thermoelectric driving wearable system according to the first treatment example in FIG. 12A with the heat source at the different temperatures, the first controlled example and the first comparison example in the stimulating time as being 30 minutes.

DETAILED DESCRIPTION

Figure 1:
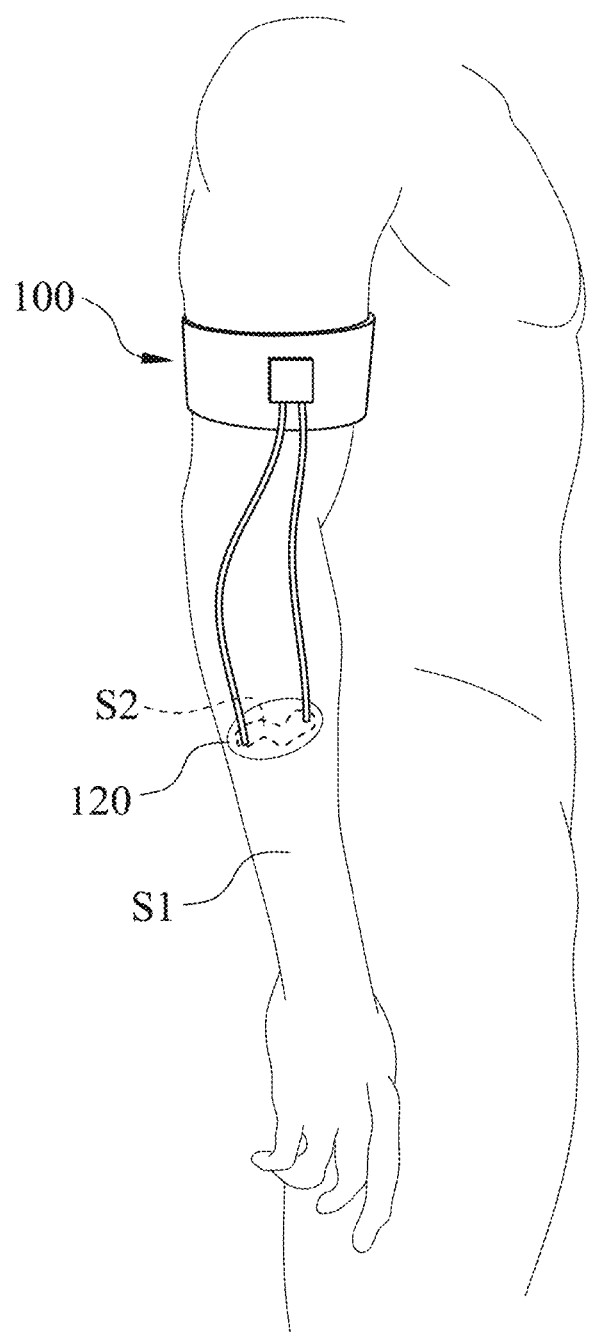
FIG. 1 shows a schematic view of a thermoelectric driving wearable system according to an embodiment of the present disclosure applied to a skin surface.
Figure 2:
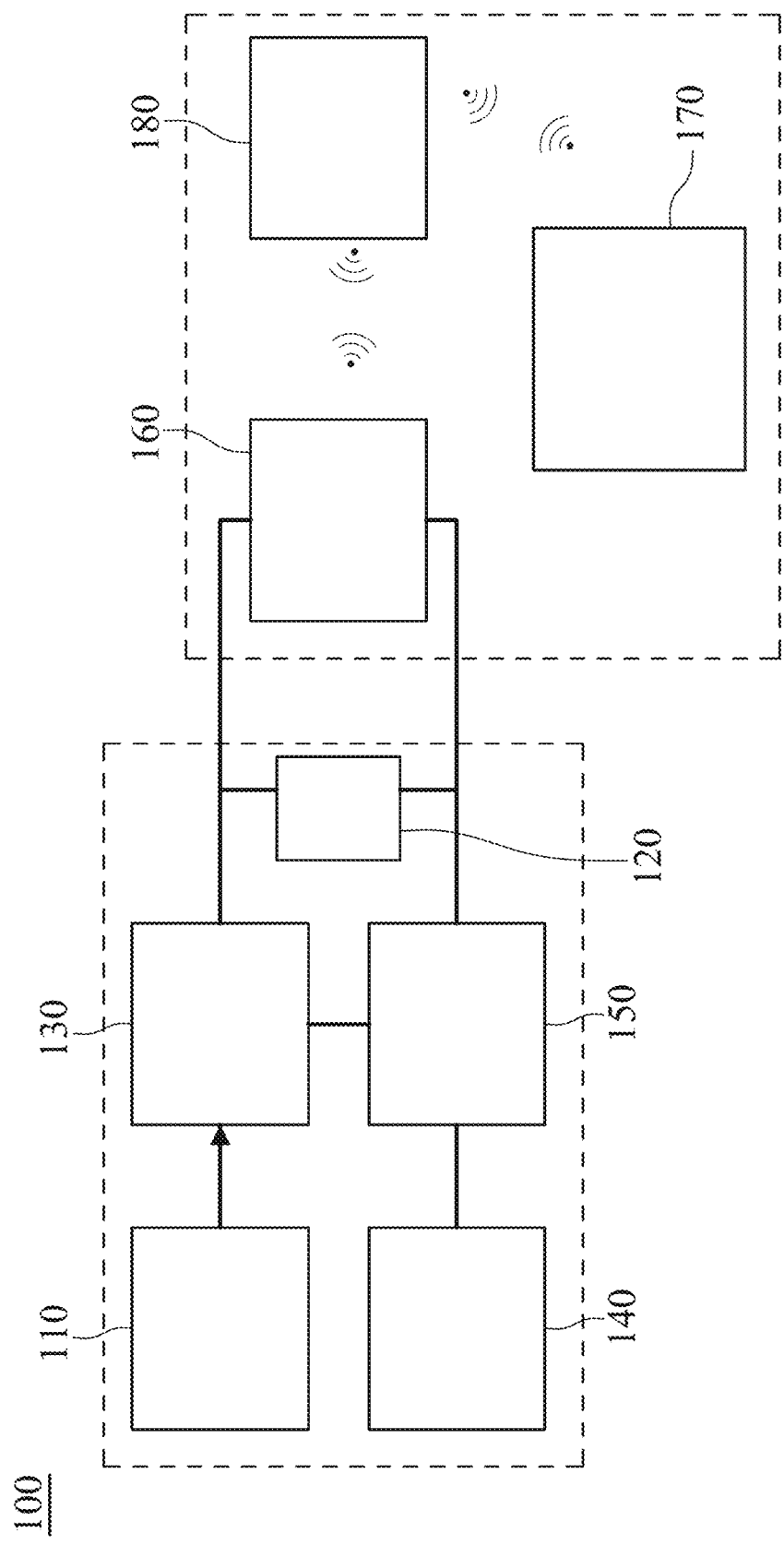
FIG. 2 shows a block diagram of the thermoelectric driving wearable system according to the embodiment in FIG. 1.

FIG. 1 shows a schematic view of a thermoelectric driving wearable system 100 according to an embodiment of the present disclosure applied to a skin surface S1. FIG. 2 shows a block diagram of the thermoelectric driving wearable system 100 according to the embodiment in FIG. 1. As shown in FIGS. 1 and 2, the thermoelectric driving wearable system 100 includes a thermoelectric device 110 and an electrical stimulating assembly 120. The thermoelectric device 110 includes two thermal interface material layers 1111, 1112 (shown in FIG. 3) and a thermoelectric converting layer 112 (shown in FIG. 3). The two thermal interface material layers 1111, 1112 are configured for contacting a heat source and a cold source, respectively. The thermoelectric converting layer 112 is located between the two thermal interface material layers 1111, 1112 and configured for generating an electric energy according to a temperature difference between the heat source and the cold source. The electrical stimulating assembly 120 is electrically connected to the thermoelectric device 110 and configured for being disposed at the skin surface S1, and the electrical stimulating assembly 120 receives the electric energy and transmits a current to a stimulated region S2.

With disposing the thermoelectric device 110 at the skin surface S1 of a user, a human body of the user may be served as the heat source to transmit a heat energy to the thermoelectric device 110 via the skin surface S1. And, an exterior environment such as air, may be served as the cold source. With the high thermal coefficient of the thermal interface material layers 1111, 1112, heat loss during heat transferring can be reduced. The thermoelectric converting layer 112 generates the electric energy according to the temperature difference between the human body and the air, and then the electrical stimulating assembly 120 receives the electric energy and transmits the current to the stimulated region S2. As shown in FIG. 1, the stimulated region S2 can be a wound on the skin surface S1, and the wound is stimulated by a mean of electrical stimulation with the current transmitted by the electrical stimulating assembly 120 to enhance curing the wound. Therefore, the thermoelectric driving wearable system 100 can provide a self-powered curing technology of electrical stimulation without an external power supply, and the power use can be improved efficiently. The details of the thermoelectric driving wearable system 100 are described in the following.

Figure 3:
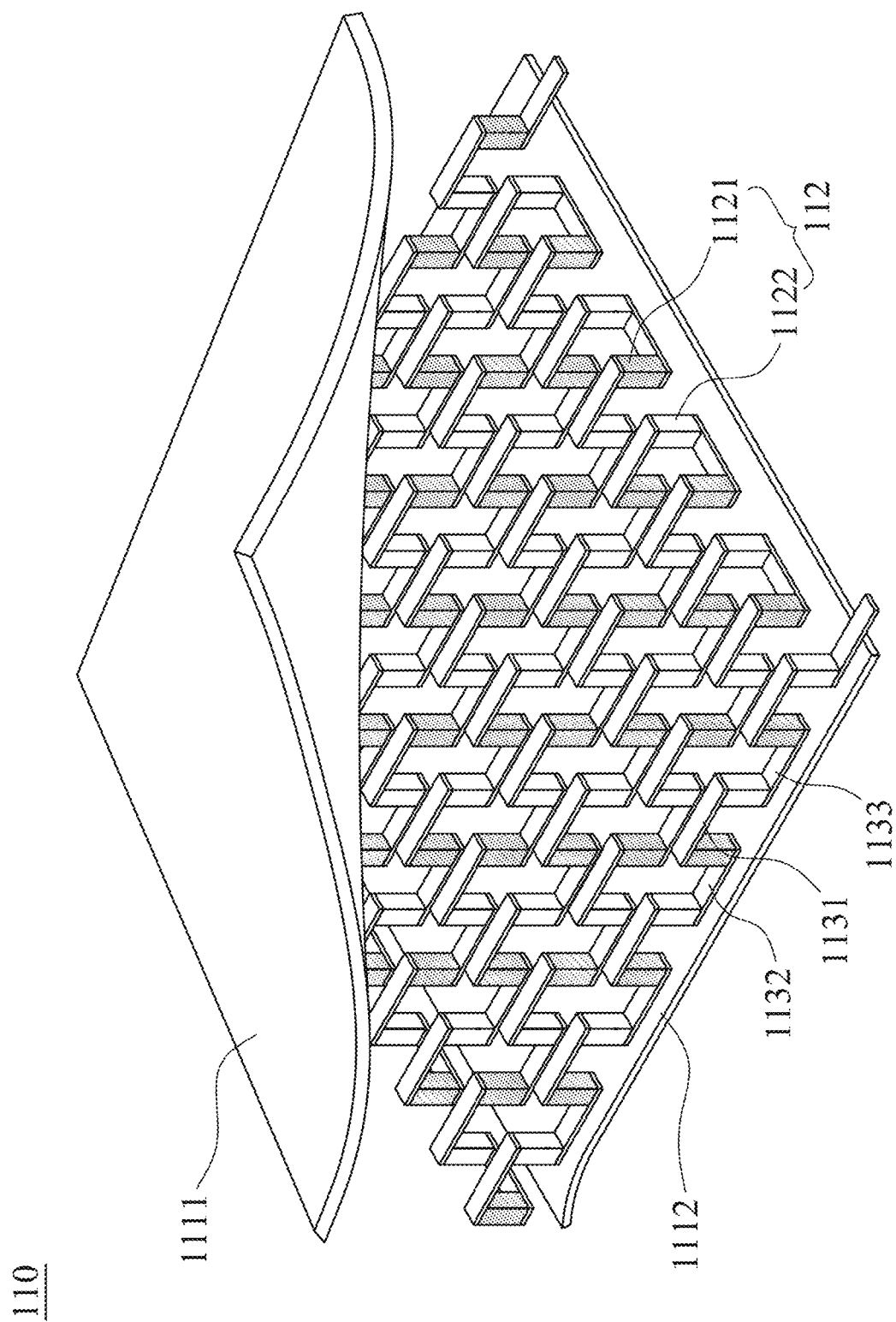
FIG. 3 shows an exploded view of the thermoelectric device according to the embodiment in FIG. 1.
Figure 4:
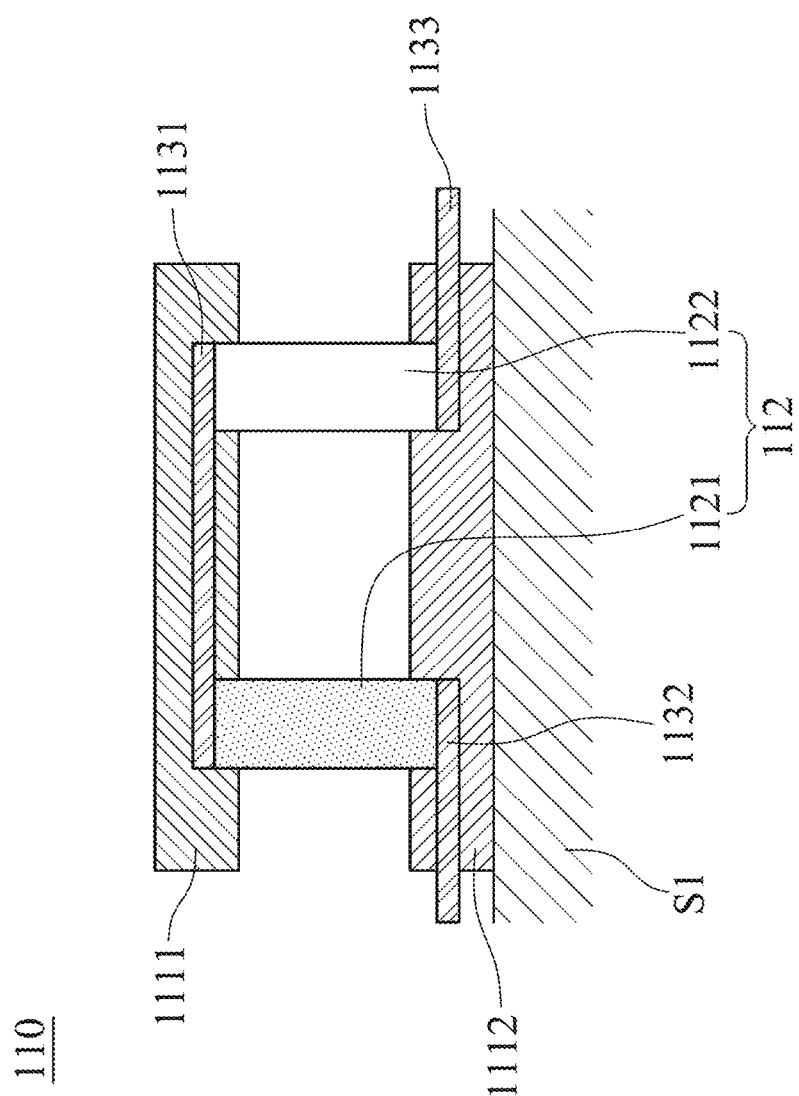
FIG. 4 shows a partial enlarged cross-sectional view of the thermoelectric device according to the embodiment in FIG. 3 disposed at the skin surface.

FIG. 3 shows an exploded view of the thermoelectric device 110 according to the embodiment in FIG. 1. FIG. 4 shows a partial enlarged cross-sectional view of the thermoelectric device 110 according to the embodiment in FIG. 3 disposed at the skin surface S1. As shown in FIGS. 1 to 4, the thermoelectric device 110 can further include a plurality of upper electrodes 1131, a plurality of first lower electrodes 1132 and a plurality of second lower electrodes 1133, the thermal interface material layer 1111 covers the upper electrodes 1131, the thermal interface material layer 1112 covers the first lower electrodes 1132 and the second lower electrodes 1133. Specifically, the thermoelectric converting layer 112 can include a plurality of N-type thermoelectric converting elements 1121 and a plurality of P-type thermoelectric converting elements 1122 which are arranged alternately to each other. Each of the upper electrodes 1131 connects an upper end of one of the N-type thermoelectric converting elements 1121 and an upper end of one of the P-type thermoelectric converting elements 1122 which is adjacent to the aforementioned one of the N-type thermoelectric converting elements 1121. Each of the first lower electrodes 1132 connects a lower end of the aforementioned one of the N-type thermoelectric converting elements 1121 and a lower end of another one of the P-type thermoelectric converting elements 1122 which is adjacent thereto. Each of the second lower electrodes 1133 connects a lower end of the aforementioned one of the P-type thermoelectric converting elements 1122 and a lower end of another one of the N-type thermoelectric converting elements 1121 which is adjacent thereto. With the upper electrodes 1131, the first lower electrodes 1132 and the second lower electrodes 1133, the N-type thermoelectric converting elements 1121 and the P-type thermoelectric converting elements 1122 are connected such that one of the N-type thermoelectric converting elements 1121 and the adjacent one of the P-type thermoelectric converting elements 1122 can form a p-n junction. Moreover, when the thermal interface material layer 1111 covers the upper electrodes 1131 and the thermal interface material layer 1112 covers the first lower electrodes 1132 and the second lower electrodes 1133, the thermoelectric converting layer 112 can be attached firmly between the two thermal interface material layers 1111, 1112 to improve efficiency of thermoelectric converting.

In the present embodiment, all of the upper electrodes 1131, the first lower electrodes 1132 and the second lower electrodes 1133 can be conductive sheets made of copper, N-type thermoelectric converting elements 1121 can be N-type doped $Bi_2Te_3$ ingots, the P-type thermoelectric converting elements 1122 can be P-typed doped $Bi_2Te_3$ ingots, and a number of the p-n junctions formed by the N-type thermoelectric converting elements 1121 and the P-type thermoelectric converting elements 1122 can be 81 pairs or 150 pairs to form a thermoelectric converting array. Each of the N-type thermoelectric converting elements 1121 and the P-type thermoelectric converting elements 1122 can be a 1.5 mm×1.5 mm×2.5 mm cuboid structure, but the present disclosure is not limited thereto. In other embodiments, each of the N-type thermoelectric converting elements and the P-type thermoelectric converting elements can be a 4 mm×4 mm×4 mm cube structure. Therefore, the thermoelectric device can be miniaturized.

Moreover, in other embodiments, the thermoelectric device can further include a heat sink element disposed between the cold source and one of the two thermal interface material layers which contacts the cold source. The heat sink element can be a fin cooling element attached to the thermal interface material layer and contacting the cold source to accelerate the heat flow between the heat source and the cold source.

Figure 5:
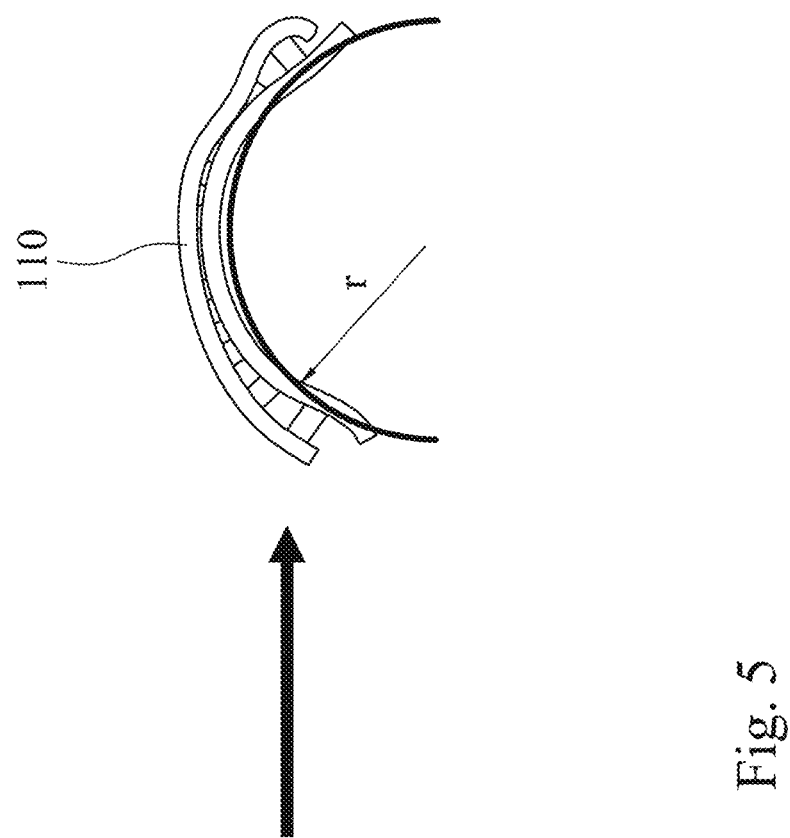
FIG. 5 shows a schematic view of the thermoelectric device according to the embodiment in FIG. 3 bended from a flat state to a bended state.
Figure 5:
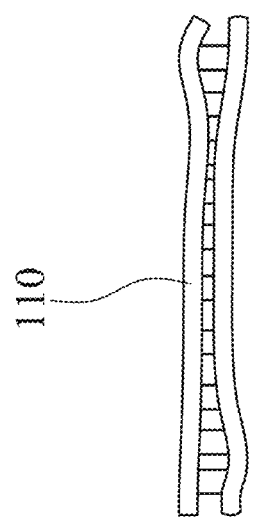
Figure 6B:
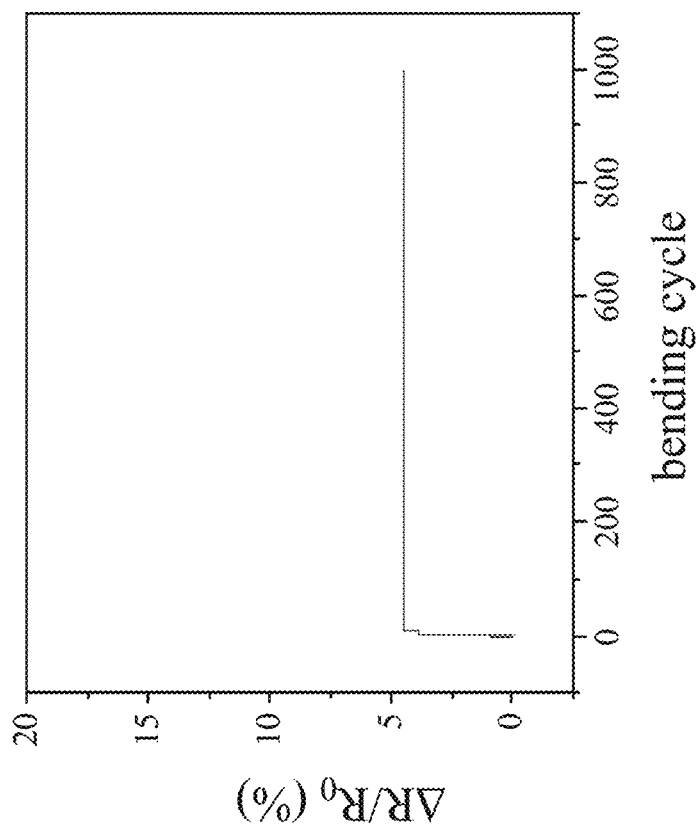
FIG. 6B shows a measurement of a relation between the electrical resistance change ratio and bending cycles of the bended thermoelectric device according to the embodiment in FIG. 5.
Figure 6A:
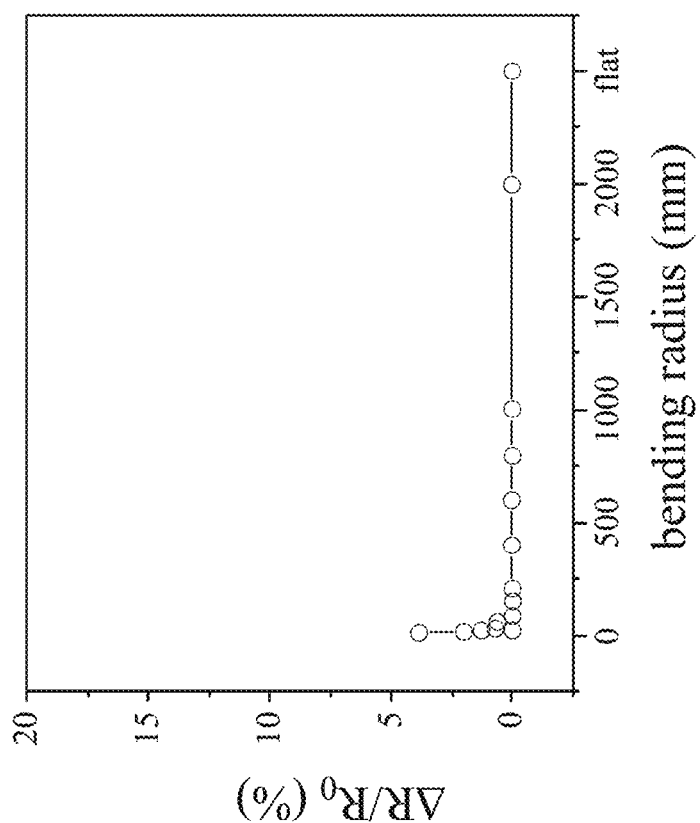
FIG. 6A shows a measurement of a relation between an electrical resistance change ratio and a bending radius of the bended thermoelectric device according to the embodiment in FIG. 5.

FIG. 5 shows a schematic view of the thermoelectric device 110 according to the embodiment in FIG. 3 bended from a flat state to a bended state. FIG. 6A shows a measurement of a relation between an electrical resistance change ratio $\Delta R/R_0$ and a bending radius r of the bended thermoelectric device 110 according to the embodiment in FIG. 5. FIG. 6B shows a measurement of a relation between the electrical resistance change ratio $\Delta R/R_0$ and bending cycles of the bended thermoelectric device 110 according to the embodiment in FIG. 5. In the embodiment of FIG. 5, each of the two thermal interface material layers 1111, 1112 can be made of an elastic material, and the elastic material is made of an aluminum nitride material or an elastic silicone composite material. In the present embodiment, each of the thermal interface material layers 1111, 1112 is made of the mixture of a silicone film and an Eco-FLEX plastic composite material. Therefore, the thermoelectric device 110 has flexibility. As shown in FIG. 5, the thermoelectric device 110 can be pressed by driving a linear motor, and then bended from the flat state to the bended state with the bending radius r without being broken. In other embodiments, the thermal interface material layers can be made of any kind of thermal interface material such as a glass slide, silicone pad or an Eco-FLEX plastic composite material, but the present disclosure is not limited thereto. Furthermore, in the electrical resistance change ratio $\Delta R/R_0$, $R_0$ represents an electrical resistance value of the thermoelectric device 110 at the flat state, and $\Delta R$ represents a difference between the electrical resistance value of the bended thermoelectric device 110 and the electrical resistance value $R_0$ of the thermoelectric device 110 at the flat state. As shown in FIG. 6A, before the bending radius r of the thermoelectric device 110 is decreased from the flat state to 30 mm, the electrical resistance change ratio $\Delta R/R_0$ of the thermoelectric device 110 keeps close to 0%, that is, the electrical resistance of the thermoelectric device 110 remains stable during bending. When the bending radius r of the thermoelectric device 110 is decreased to 30 mm, the electrical resistance change ratio $\Delta R/R_0$ of the thermoelectric device 110 raises to 1%, and 30 mm is the bending radius r when the thermoelectric driving wearable system 100 is worn on the skin surface S1 of the human body. Moreover, when the thermoelectric device 110 is bended to the bended state with the bending radius r being 10 mm, the electrical resistance change ratio $\Delta R/R_0$ of the thermoelectric device 110 raises to 4.44%, and 10 mm is a curvature of bending a human finger. As shown in FIG. 6B, the thermoelectric device 110 is bended repeatedly to the bended state with the bending radius r being 10 mm and the electrical resistance change ratio $\Delta R/R_0$ is measured. After repeatedly bending the thermoelectric device 110 for 1000 bending cycles, the electrical resistance change ratio $\Delta R/R_0$ of the thermoelectric device 110 keeps around 4.44%, and the electrical resistance of the thermoelectric device 110 remains stable.

Figure 7:
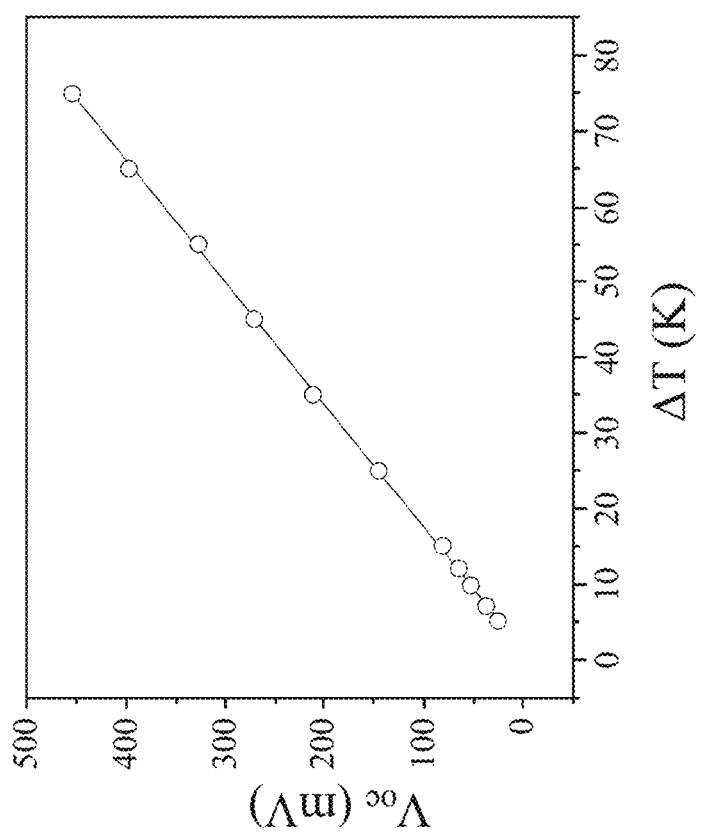
FIG. 7 shows a relation between an open-circuit voltage of the thermoelectric device according to the embodiment in FIG. 3 and a temperature difference between the heat source and the cold source.

FIG. 7 shows a relation between an open-circuit voltage $V_{OC}$ of the thermoelectric device 110 according to the embodiment in FIG. 3 and a temperature difference between the heat source and the cold source. As shown in FIG. 7, the open-circuit voltage $V_{OC}$ between the two thermal interface material layers 1111, 1112 of the thermoelectric device 110 is positively proportional to the temperature difference $\Delta T$ between the heat source and the cold source, and Seebeck coefficient of the thermoelectric device 110 can be obtained as 6.17 mV/K.

Figure 8:
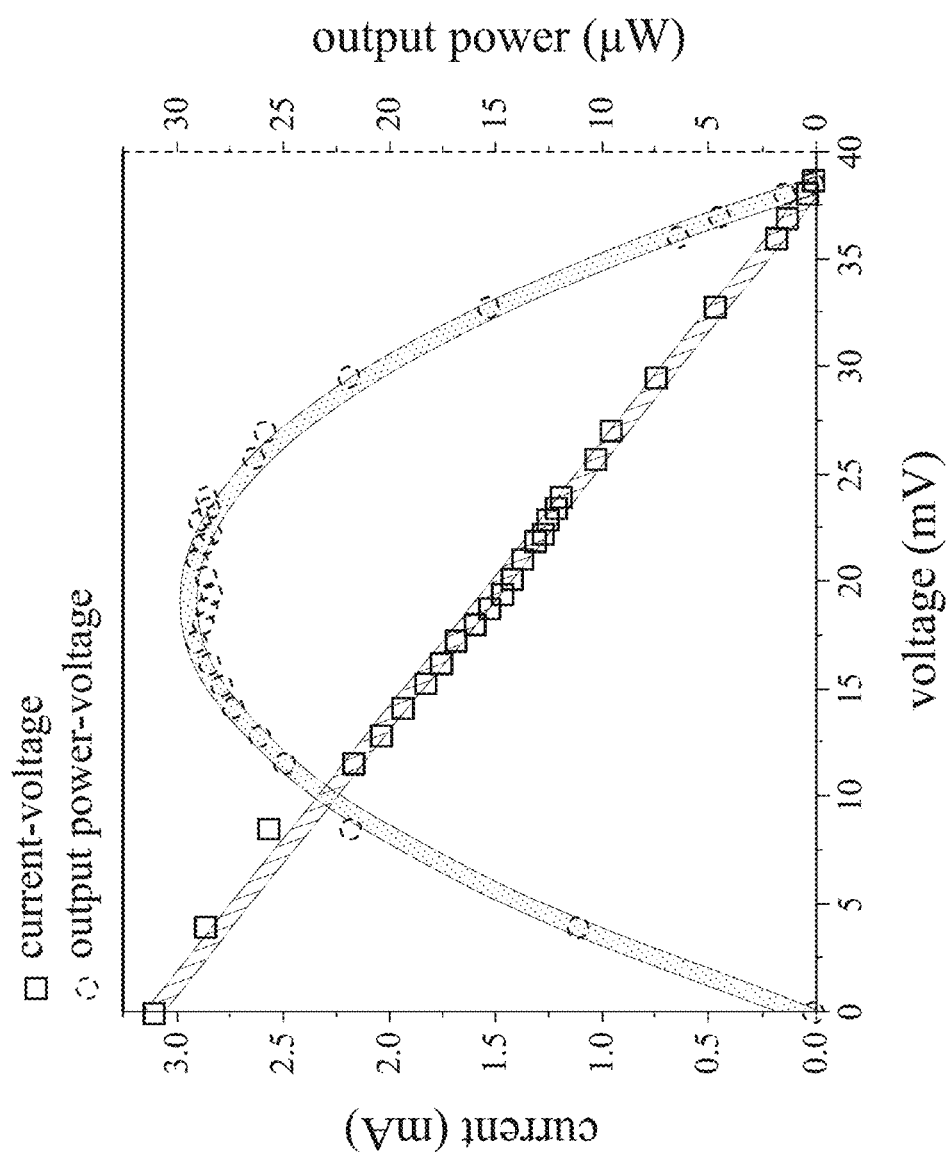
FIG. 8 shows a relation between an output power and a voltage and a relation between a current and the voltage of the thermoelectric device according to the embodiment in FIG. 3.

FIG. 8 shows a relation between an output power and a voltage and a relation between a current and the voltage of the thermoelectric device 110 according to the embodiment in FIG. 3. The relation between the output power and the voltage and the relation between the current and the voltage are measured under the condition that the temperature of the air is 298 K and the temperature difference between the heat source (the temperature of the skin surface S1) and the air is 7K. By connecting the thermoelectric device 110 to a tunable resistance, the output power, current and voltage can be measured by tuning the electrical resistance. As shown in FIG. 8, a maximum value of the output power of the thermoelectric device 110 is 29.47 µW which is enough to drive other Internet of Things (IOT) devices necessary to the thermoelectric device 110.

Figure 9:
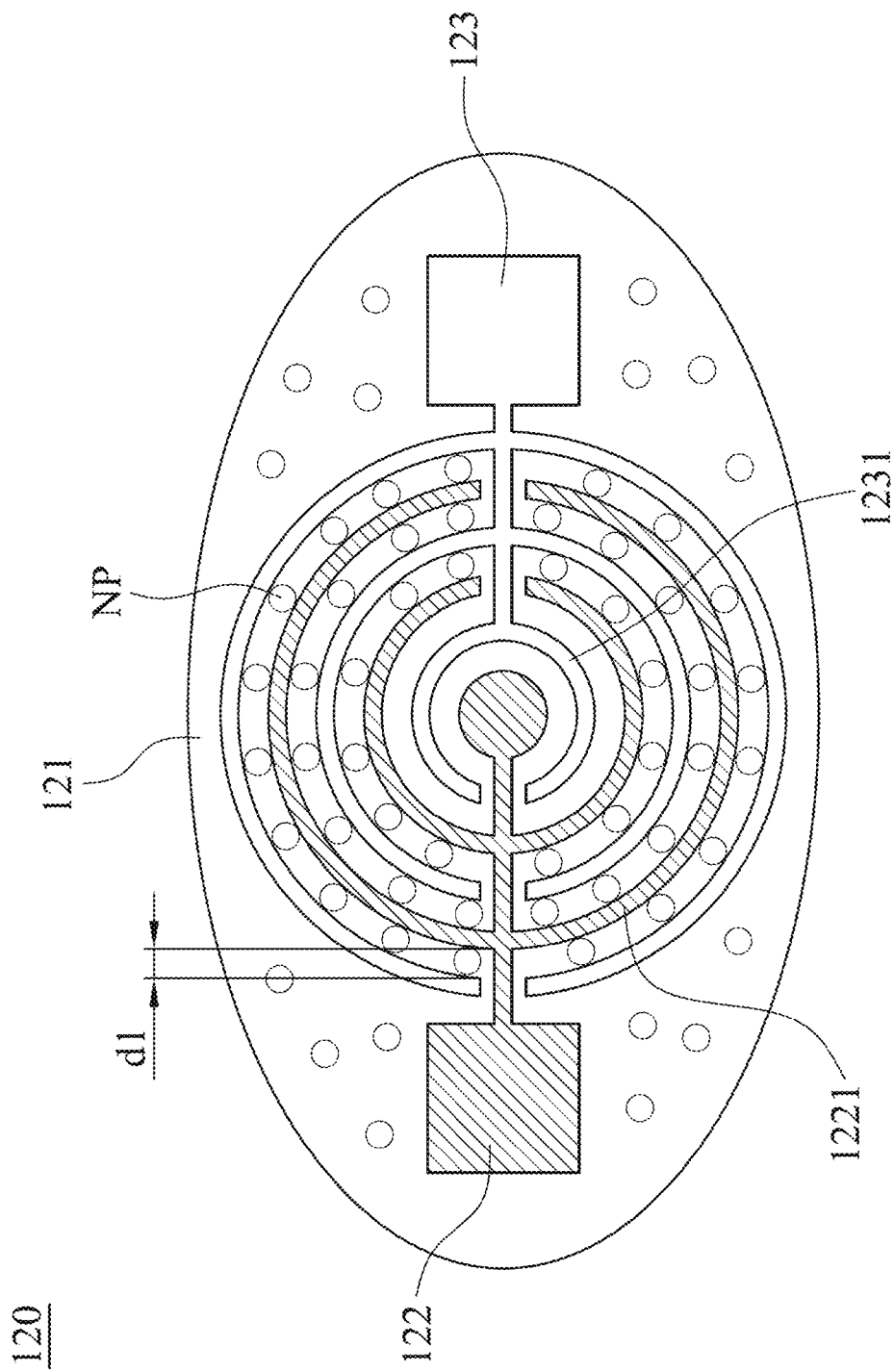
FIG. 9 shows a schematic view of the electrical stimulating assembly according to the embodiment in FIG. 2.

FIG. 9 shows a schematic view of the electrical stimulating assembly 120 according to the embodiment in FIG. 2. As shown in FIG. 9, the electrical stimulating assembly 120 can include a cover membrane 121, a first electrode assembly 122 and a second electrode assembly 123. The cover membrane 121 is configured for covering the stimulated region S2. Specifically, the cover membrane 121 can be a membrane made of polyimide (PI) such as KAPTON, or a membrane made of polyethylene terephthalate (PET), but the present disclosure is not limited thereto. The first electrode assembly 122 is disposed on the cover membrane 121, electrically connected to a positive electrode and has a plurality of first comb electrodes 1221, and the first comb electrodes 1221 are configured for contacting the stimulated region S2. The second electrode assembly 123 is disposed on the cover membrane 121, electrically connected to a negative electrode, the second electrode assembly 123 has a plurality of second comb electrodes 1231, and the second comb electrodes 1231 are configured for contacting the stimulated region S2. The first comb electrodes 1221 are electrically isolated from the second comb electrodes 1231, and the first comb electrodes 1221 and the second comb electrodes 1231 form a current stimulating region (that is, the region of the first comb electrodes 1221 and the second comb electrodes 1231 contacting the stimulating region S2 is the current stimulating region). By the configuration of the comb electrodes, the area of the stimulating region S2 stimulated by the current can be increased to improve efficiency of electrical stimulation.

Furthermore, the first electrode assembly 122 and the second electrode assembly 123 can be made of gold, and each of the first electrode assembly 122 and the second electrode assembly 123 can be doped by a plurality of nanoparticles NP, and the nanoparticles NP are selected from iron (Fe), cupper (Cu), magnesium (Mg), manganese (Mn), calcium (Ca), potassium (K), aluminum (Al), selenium (Se), and a group composed of a combination thereof. By doping the nanoparticles NP between the first electrode assembly 122 and the second electrode assembly 123, anti-inflammatory can be provided. In the embodiment of FIG. 9, each of the nanoparticles NP is a selenium nanoparticle, but the present disclosure is not limited thereto. Therefore, the wound curing of the stimulating region S2 can be further enhanced.

Furthermore, an electrode distance dl is included between each of the first comb electrodes 1221 and each of the second comb electrodes 1231 which is adjacent thereto, and the electrode distance dl is ranged between 1 mm-6 mm. The current stimulating region formed by the first comb electrodes 1221 and the second comb electrodes 1231 is a round region, and each of the first comb electrodes 1221 and each of the second comb electrodes 1231 which is adjacent thereto form a plurality of concentric circular sections with different diameters. Therefore, the wound curing can be further accelerated.

Figure 10:
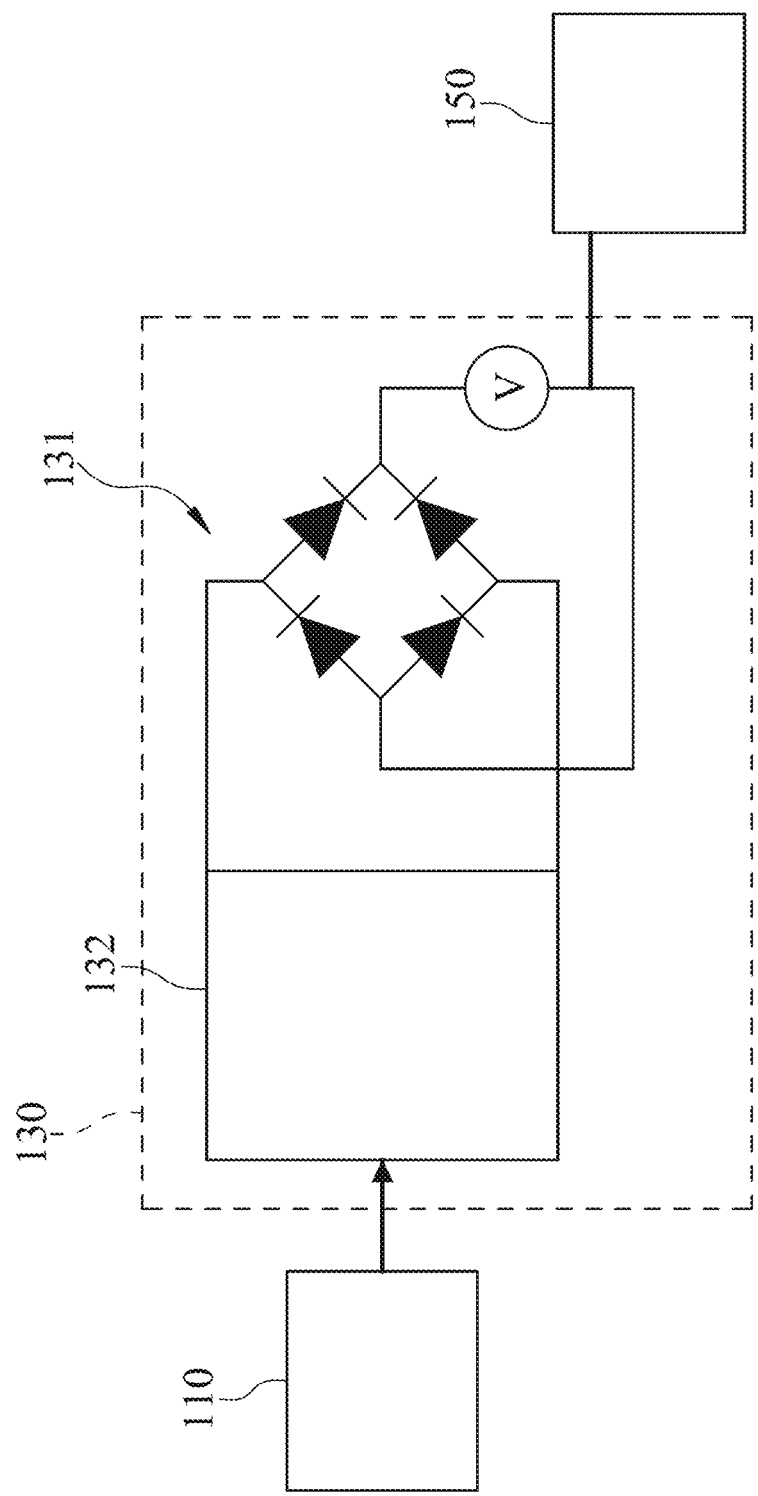
FIG. 10 shows a schematic view of the thermoelectric device, a boosting and rectifying module and a controlling module according to the embodiment in FIG. 2.

FIG. 10 shows a schematic view of the thermoelectric device 110, a boosting and rectifying module 130 and a controlling module 150 according to the embodiment in FIG. 2. As shown in FIGS. 2 and 10, the thermoelectric driving wearable system 100 can further include the boosting and rectifying module 130, a pulse generating module 140, the controlling module 150 and a monitoring module 160. The boosting and rectifying module 130 is electrically connected between the thermoelectric device 110 and the electrical stimulating assembly 120, the boosting and rectifying module 130 is configured for converting the electric energy from an alternate current form to a direct current form, and modulating a voltage value of the electric energy. The boosting and rectifying module 130 can include a rectifier 131 and a booster 132. The booster 132 is electrically connected to the thermoelectric device 110. The rectifier 131 is electrically connected between the booster 132 and the controlling module 150. The pulse generating module 140 is electrically connected to the controlling module 150, and the pulse generating module 140 is configured for turning on the controlling module 150 to turn on the electrical stimulating assembly 120 intermittently according to a pulse duration, and the pulse duration is ranged between 50 ms-200 ms. The controlling module 150 is electrically connected between the boosting and rectifying module 130 and the electrical stimulating assembly 120. The pulse generating module 140 transmits a pulse signal having the pulse duration. When the controlling module 150 receives the pulse signal, the controlling module 150 opens a circuit of the boosting and rectifying module 130 and the electrical stimulating assembly 120 such that the electrical stimulating assembly 120 can transmit the current to the stimulating region S2; when the controlling module 150 does not receive the pulse signal, the controlling module 150 closes the circuit to stop the current from flowing into the electrical stimulating assembly 120. The monitoring module 160 is configured for detecting a resistance value of the stimulated region S2 and estimating a recovery level of the stimulated region S2 according to a ratio between the resistance value of the stimulated region S2 and a resistance value of a normal skin, and the monitoring module 160 transmits a monitoring signal to an electronic device 170. Furthermore, the resistance value of the normal skin is the resistance value of unwound part of the skin surface S1 of the user. Moreover, the monitoring module 160 can transmit the monitoring signal wirelessly to a base station 180 first, and then to the electronic device 170. Therefore, a distance of the electronic device 170 receiving the monitoring signal can be increased.

Figure 11B:
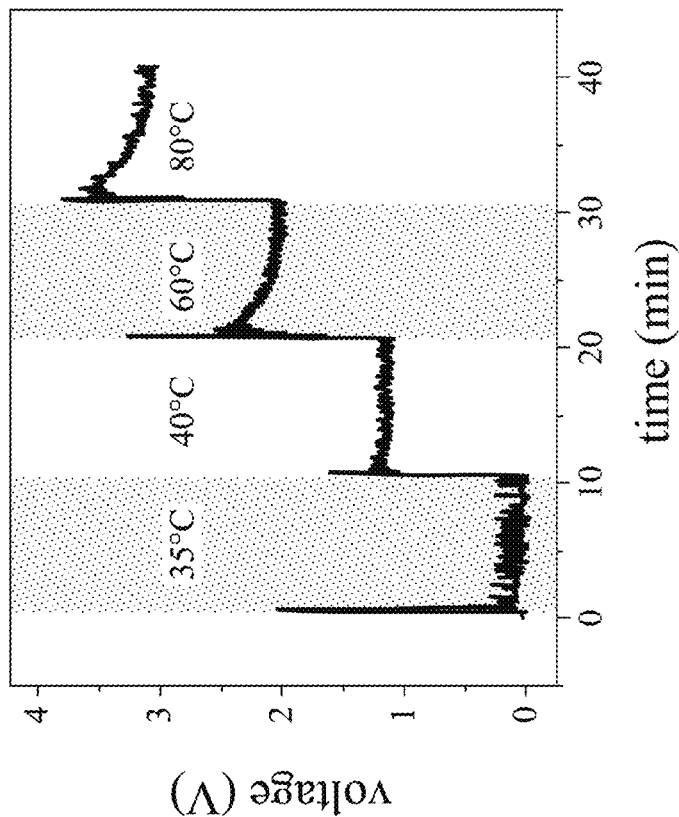
FIG. 11B shows a measurement of the voltage value of the electric energy and time of the thermoelectric device after boosted by the booster according to the embodiment in FIG. 10.
Figure 11A:
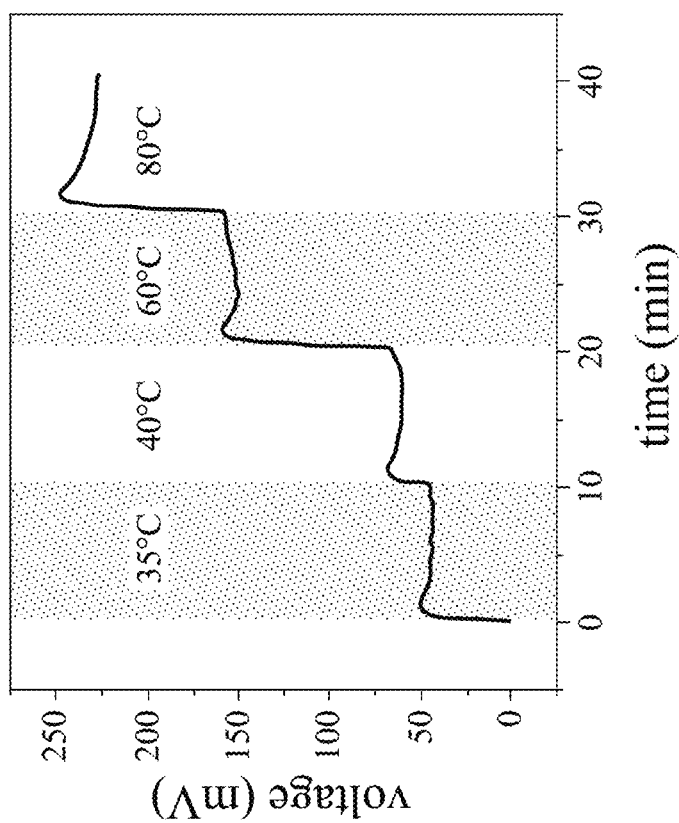
FIG. 11A shows a measurement of a voltage value of the electric energy and time of the thermoelectric device before boosted by the booster according to the embodiment in FIG. 10.

FIG. 11A shows a measurement of a voltage value of the electric energy and time of the thermoelectric device 110 before boosted by the booster 132 according to the embodiment in FIG. 10. FIG. 11B shows a measurement of the voltage value of the electric energy and time of the thermoelectric device after boosted by the booster 132 according to the embodiment in FIG. 10. As shown in FIG. 11A, the booster 132 does not boost the voltage such that the electric energy generated by the thermoelectric device 110 can be converted from the alternate current form to the direct current form, and then the voltage value is measured at every 10 minutes with changing the temperature of the heat source. Minimum values of the voltage values at the temperatures of the heat source as 35° C., 40° C., 60° C. and 80° C. are 43.6 mV, 67.9 mV, 158.6 mV and 227.2 mV, respectively. As shown in FIG. 11A, the voltage values at 35° C. and 40° C. can be output stably. As shown in FIG. 11B, the electric energy generated by the thermoelectric device 110 is boosted by the booster 132 first, then converted by the rectifier 131, and then measured. Minimum values of the voltage values at the temperatures of the heat source as 35° C., 40° C., 60° C. and 80° C. are boosted to 0.07 V, 1.09 V, 1.96 V and 3.01 V, respectively. As known in FIG. 11B, the voltage values of the thermoelectric device 110 at the temperatures of the heat source as 35° C. and 40° C. can be output stably. When the temperature of the heat source is close to the temperature of the human body (35° C.-40° C.), the voltage value of the thermoelectric device 110 after boosting remains stable.

In other embodiments, the boosting and rectifying module can be a LTC3108 boosting and rectifying circuit which can boost and rectify the voltage value of the electric energy generated by the thermoelectric device, and the voltage value is ranged between 2 V to 5 V. Specifically, the boosting and rectifying module 130 can boost the voltage value to 2.35 V, 3.3 V, 4.1 V or 5V.

In the following first treatment example to fifth treatment example, the structure and configuration of the thermoelectric driving wearable system is similar to the thermoelectric driving wearable system 100 in FIG. 1, and, in the first treatment example to fourth treatment example, the electrical stimulating assembly of the thermoelectric driving wearable system is configured for transmitting a current to a stimulated region, and the stimulated region is a cell culture plate of NIH 3T3 cells. The cell viability of NIH 3T3 cells is increased by electrical stimulation. First to fourth controlled examples CT are cell culture plates of NIH 3T3 cells without any stimulation to be compared with the treatment examples. First to fourth comparison examples ED are ell culture plates of NIH 3T3 cells stimulated by transmitting the current with the conventional electrodes. In detail, NIH 3T3 cell is an embryonic fibroblasts cell of a laboratory rat, which is not described in detail hereinafter. In the fifth treatment example, the thermoelectric driving wearable system is configured for transmitting the current to the stimulated region, and the stimulated region is a wound area on a skin surface of a mouse. A fifth controlled example CT is a wound area without any stimulation to be compared with the treatment example. A fifth comparison example ED is a wound area stimulated by electrodes directly.

First Treatment Example

FIG. 12A shows a measurement of cell viabilities of a thermoelectric driving wearable system according to a first treatment example of the present disclosure with the heat source at the different temperatures HT1, HT2, HT3, HT4, a first controlled example CT and a first comparison example ED in the stimulating time as being 10 minutes. FIG. 12B shows a measurement of the cell viabilities of the thermoelectric driving wearable system according to the first treatment example in FIG. 12A with the heat source at the different temperatures HT1, HT2, HT3, HT4, the first controlled example CT and the first comparison example ED in the stimulating time as being 15 minutes. FIG. 12C shows a measurement of the cell viabilities of the thermoelectric driving wearable system according to the first treatment example in FIG. 12A with the heat source at the different temperatures HT1, HT2, HT3, HT4, the first controlled example CT and the first comparison example ED in the stimulating time as being 30 minutes. As shown in FIG. 12A, during the stimulating time as being 10 minutes, the thermoelectric driving wearable system with the heat source at the different temperatures HT1, HT2, HT3, HT4 and the cold source in the same temperature transmits the current to stimulate the cell culture plate of NIH 3T3 cells continuously. The temperatures HT1, HT2, HT3, HT4 of the heat source are 35° C., 40° C., 60° C. and 80° C., respectively, and the temperature of the cold source is 0° C. As known in FIG. 12A, the cell viabilities of NIH 3T3 cells of the first comparison example ED and the thermoelectric driving wearable system with the heat source at the temperature HT4 are smaller than the cell viability of NIH 3T3 cells of the first controlled example after simulating 10 minutes. As shown in FIG. 12B, the cell viabilities of NIH 3T3 cells of the thermoelectric driving wearable system with the heat source at the temperatures HT1, HT2, HT3, HT4 are higher than the cell viability of the first controlled example CT after simulating 15 minutes. As shown in FIG. 12C, the cell viabilities of the first comparison example ED and the thermoelectric driving wearable system with the heat source at the temperatures HT1, HT2, HT3, HT4 are smaller than the cell viability of the first controlled example CT after simulating 30 minutes. Furthermore, when the temperature of the heat source is 40° C. and the stimulating time is 15 minutes, the cell viability of NIH 3T3 cells of the thermoelectric driving wearable system can reach to 117% to achieve the ability of curing wounds; however, when the temperature of the heat source is too high, cells cannot endure the overwhelming high voltage value and electric field strength, and it leads to death of parts of the cells.

Second Treatment Example

Figures 13A, 13B, 13C:
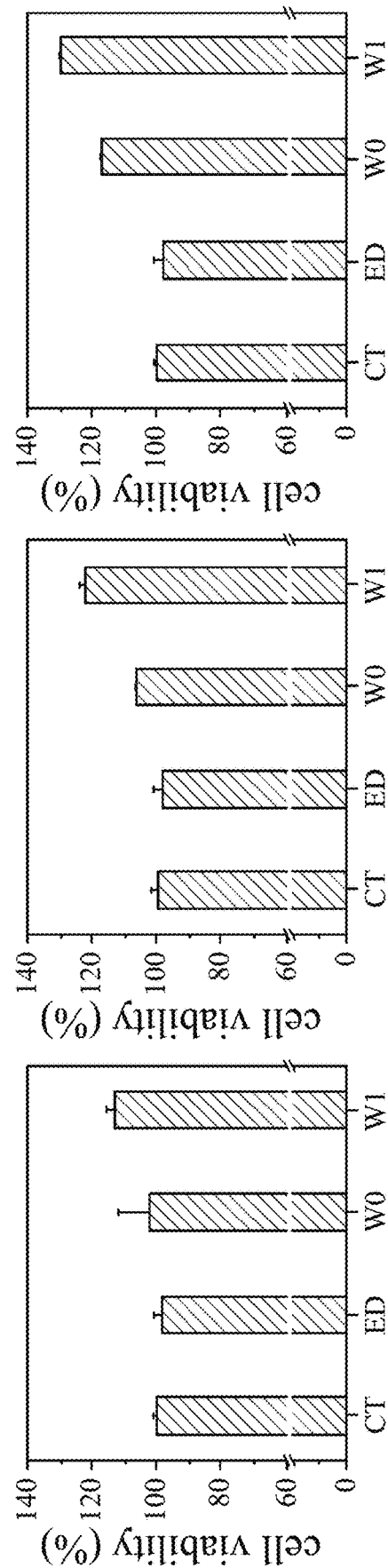
FIG. 13A shows a measurement of the cell viabilities of the thermoelectric driving wearable system according to a second treatment example of the present disclosure at a boosted state and an unboosted state with the electrode distance as being 6 mm, a second controlled example and a second comparison example.
FIG. 13B shows a measurement of the cell viabilities of the thermoelectric driving wearable system according to a second treatment example in FIG. 13A at the boosted state and the unboosted state with the electrode distance as being 3 mm, the second controlled example and the second comparison example.
FIG. 13C shows a measurement of the cell viabilities of the thermoelectric driving wearable system according to a second treatment example in FIG. 13A at the boosted state and the unboosted state with the electrode distance as being 1 mm, the second controlled example and the second comparison example.

FIG. 13A shows a measurement of the cell viabilities of the thermoelectric driving wearable system according to a second treatment example of the present disclosure at a boosted state W1 and an unboosted state W0 with the electrode distance as being 6 mm, a second controlled example CT and a second comparison example ED. FIG. 13B shows a measurement of the cell viabilities of the thermoelectric driving wearable system according to a second treatment example in FIG. 13A at the boosted state W1 and the unboosted state W0 with the electrode distance as being 3 mm, the second controlled example CT and the second comparison example ED. FIG. 13C shows a measurement of the cell viabilities of the thermoelectric driving wearable system according to a second treatment example in FIG. 13A at the boosted state W1 and the unboosted state W0 with the electrode distance as being 1 mm, the second controlled example CT and the second comparison example ED. The electrode distance of the thermoelectric driving wearable system can be adjusted, and the electrode distance is adjusted to 6 mm, 3 mm, or 1 mm, respectively. Moreover, the temperatures of the heat source and the cold source contacting the thermoelectric driving wearable system are 40° C. and 0° C., respectively, and the stimulating time of the thermoelectric driving wearable system and the second comparison example ED contacting and stimulating NIH 3T3 cells is 15 minutes. As shown in FIG. 13A, the boosting and rectifying module of the thermoelectric driving wearable system can boost the voltage value of the electric energy from the unboosted state W0 to the boosted state W1 to measure the voltage value, and the cell viability of NIH 3T3 cells of the thermoelectric driving wearable system at the boosted state W1 with the electrode distance as 6 mm is apparently higher than that of the cell viabilities of the second controlled example CT and the second comparison example ED. Moreover, as shown in FIGS. 13A to 13C, when the electrode distance is decreased from 6 mm, 3 mm to 1 mm, the cell viability of NIH 3T3 cells of the thermoelectric driving wearable system at the boosted state W1 or the unboosted state W0 can be increased gradually. When the thermoelectric driving wearable system is at the boosted state W1 and the electrode distance is 1 mm, the cell viability of NIH 3T3 cells can reach to 129%. By decreasing the electrode distance, the wound curing can further be accelerated.

Third Treatment Example

Figure 14B:
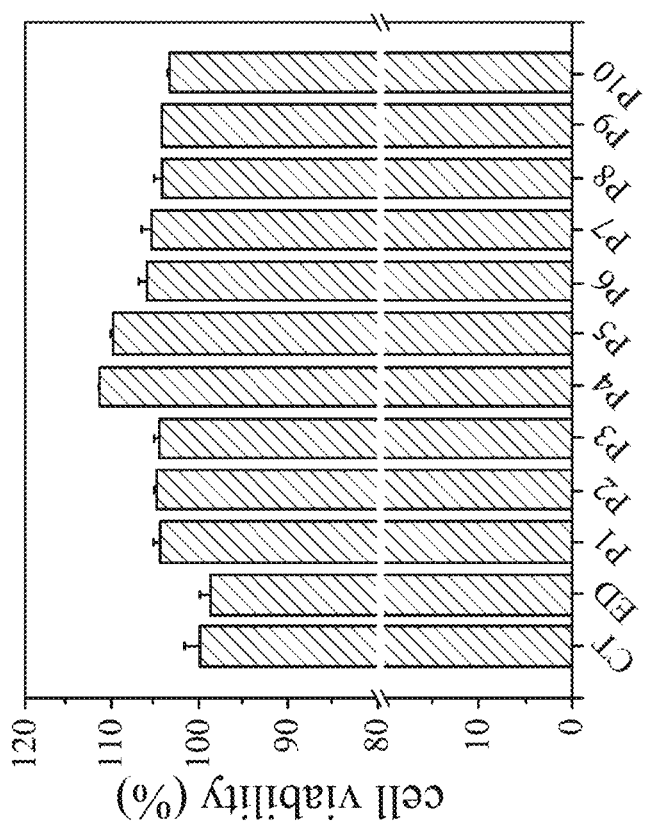
FIG. 14B shows a measurement of the cell viabilities of the thermoelectric driving wearable system according to the third treatment example with different pulse durations, the third controlled example and the third comparison example.
Figure 14A:
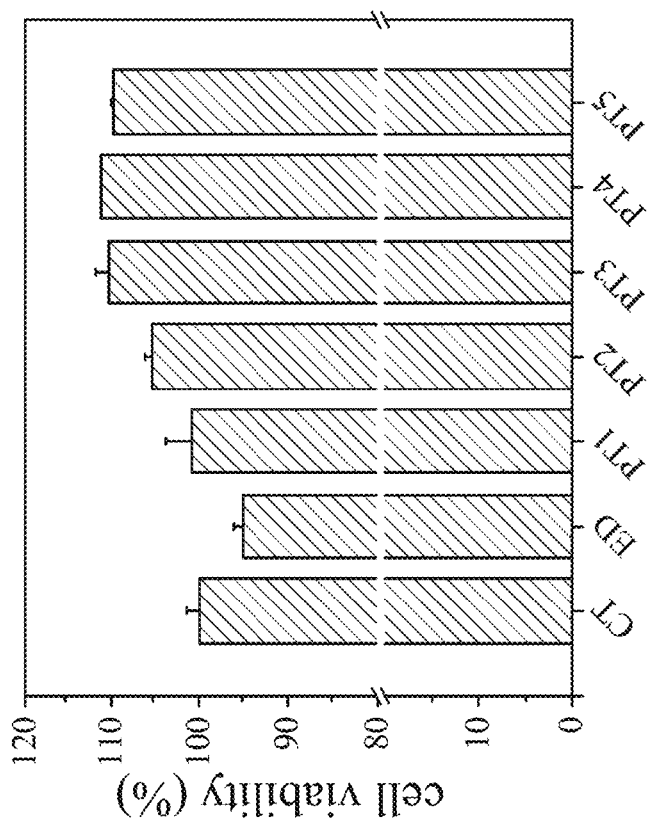
FIG. 14A shows a measurement of the cell viabilities of the thermoelectric driving wearable system according to a third treatment example of the present disclosure with different pulse frequencies, a third controlled example and a third comparison example.
Figure 14C:
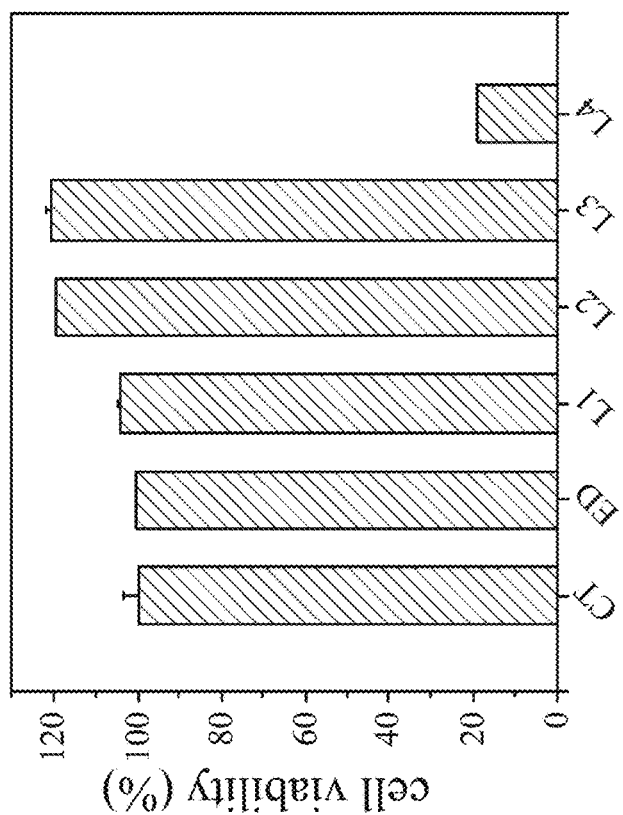
FIG. 14C shows a measurement of the cell viabilities of the thermoelectric driving wearable system according to the third treatment example with different stimulating times, the third controlled example and the third comparison example.
Figure 14D:
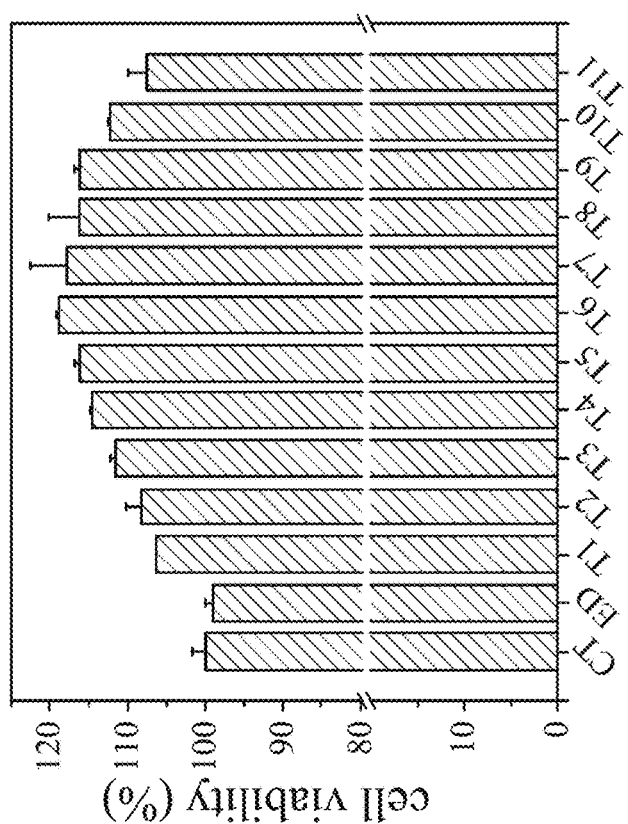
FIG. 14D shows a measurement of the cell viabilities of the thermoelectric driving wearable system according to the third treatment example with different voltage values, the third controlled example and the third comparison example.

FIG. 14A shows a measurement of the cell viabilities of the thermoelectric driving wearable system according to a third treatment example of the present disclosure with different pulse frequencies P1, P2, P3, P4, P5, P6, P7, P8, P9, P10, a third controlled example CT and a third comparison example ED. FIG. 14B shows a measurement of the cell viabilities of the thermoelectric driving wearable system according to the third treatment example with different pulse durations PT1, PT2, PT3, PT4, PT5, the third controlled example CT and the third comparison example ED. FIG. 14C shows a measurement of the cell viabilities of the thermoelectric driving wearable system according to the third treatment example with different stimulating times T1, T2, T3, T4, T5, T6, T7, T8, T10, T11, the third controlled example CT and the third comparison example ED. FIG. 14D shows a measurement of the cell viabilities of the thermoelectric driving wearable system according to the third treatment example with different voltage values L1, L2, L3, L4, the third controlled example CT and the third comparison example ED. The pulse generating module of the thermoelectric driving wearable system turns on the electrical stimulating assembly 120 intermittently according to a pulse duration and a pulse frequency, the pulse duration is ranged between 50 ms to 200 ms, and the boosting and rectifying module can adjust the voltage value of the electric energy ranged between 2 V and 5 V. As shown in FIGS. 14A to 14D, via measuring the cell viabilities of NIH 3T3 cells stimulated by the thermoelectric driving wearable system with different pulse durations, pulse frequencies, stimulating times and voltage values sequentially, the best condition which the thermoelectric driving wearable system stimulates NIH 3T3 cells can be obtained.

As shown in FIG. 14A, the pulse generating module can generate the pulse signal to controlling module to control the electrical stimulating assembly to transmit the current according to the pulse frequencies P1, P2, P3, P4, P5, P6, P7, P8, P9, P10, and the pulse frequencies P1, P2, P3, P4, P5, P6, P7, P8, P9, P10 are 1 Hz, 2 Hz, 3 Hz, 4 Hz, 5 Hz, 6 Hz, 7 Hz, 8 Hz, 9 Hz and 10 Hz, respectively. By the measurement, in the condition that the stimulating time is 10 s and the voltage value is 3.3 V, the cell viability of NIH 3T3 cells stimulated by the thermoelectric driving wearable system at the pulse frequency P4 (4 Hz) is higher than the cell viabilities of the thermoelectric driving wearable system at the pulse frequencies P1, P2, P3, P5, P6, P7, P8, P9, P10, the third controlled example CT and the third comparison example ED.

As shown in FIG. 14B, the pulse generating module can turn on the electrical stimulating assembly according to the pulse durations PT1, PT2, PT3, PT4, PT5, and the pulse durations PT1, PT2, PT3, PT4, PT5 are 50 ms, 100 ms, 125 ms, 150 ms and 200 ms, respectively. By the measurement, in the condition that the stimulating time is 10 s, the pulse frequency is 4 Hz and the voltage value is 3.3 V, the cell viability of NIH 3T3 cells stimulated by the thermoelectric driving wearable system at the pulse duration PT4 (150 ms) is higher than the cell viabilities of the thermoelectric driving wearable system at the pulse durations PT1, PT2, PT3, PT5, the third controlled example CT and the third comparison example ED.

As shown in FIG. 14C, the electrical stimulating assembly of the thermoelectric driving wearable system provides the current to stimulate the stimulated region (the cell culture plate of NIH 3T3 cells) according to an electrically stimulating frequency. Furthermore, based on the condition of the user, the thermoelectric driving wearable system can stimulate the stimulated region according to a stimulating time every day.

As shown in FIG. 14C, the thermoelectric driving wearable system can stimulate NIH 3T3 cells in the stimulating times T1, T2, T3, T4, T5, T6, T7, T8, T9, T10, T11, and the stimulating times T1, T2, T3, T4, T5, T6, T7, T8, T9, T10, T11 are 10 s, 15 s, 20 s, 25 s, 30 s, 35 s, 40 s, 45 s, 50 s, 55 s and 60 s, respectively. By the measurement, in the condition that the pulse frequency is 4 Hz and the voltage value is 3.3 V, the cell viability of NIH 3T3 cells stimulated by the thermoelectric driving wearable system in the stimulating time T6 (35 s) is higher than the cell viabilities of the thermoelectric driving wearable system in the stimulating times T1, T2, T3, T4, T5, T7, T8, T9, T10, T11, the third controlled example CT and the third comparison example ED. As known in FIG. 14C, when the electrically stimulating frequency of the thermoelectric driving wearable system is 35 s per day, the cell viability can be further increased to improve wound curing.

As shown in FIG. 14D, the boosting and rectifying module of the thermoelectric driving wearable system can adjust the voltage values L1, L2, L3, L4 of the electric energy to stimulate NIH 3T3 cells, and the voltage values L1, L2, L3, L4 are 2.35 V, 3.3 V, 4.1 V and 5.0 V, respectively. By the measurement, in the condition that the pulse frequency is 4 Hz, the voltage value is 3.3 V and the stimulating time is 35 s, the cell viabilities of NIH 3T3 cells stimulated by the thermoelectric driving wearable system at the voltage value L2 (3.3 V) and the voltage value L3 (4.1 V) are higher than the cell viabilities of the thermoelectric driving wearable system at the voltage values L1, L4, the third controlled example CT and the third comparison example ED.

Figure 15:
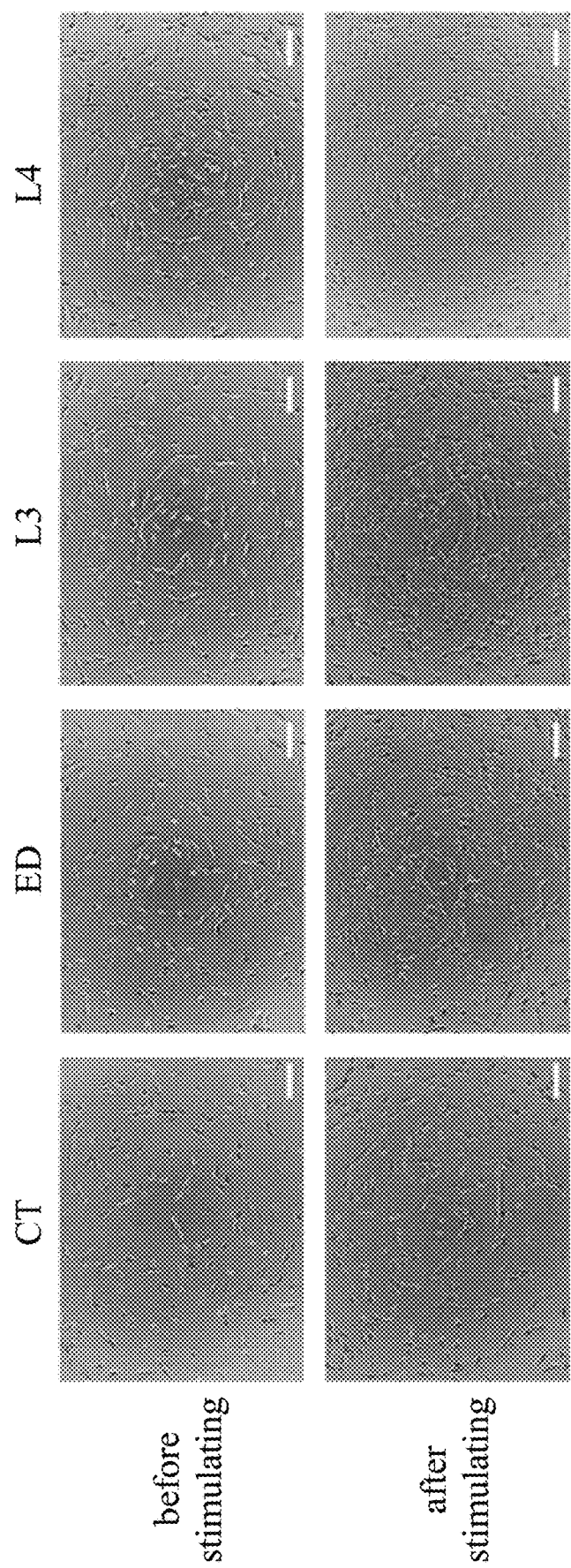
FIG. 15 shows a comparison view of cell numbers of NIH 3T3 cells stimulated by the thermoelectric driving wearable system according to the third treatment example in FIG. 14D with the different voltage values, the third controlled example and the third comparison example.

FIG. 15 shows a comparison view of cell numbers of NIH 3T3 cells stimulated by the thermoelectric driving wearable system according to the third treatment example in FIG. 14D with the different voltage values L3, L4, the third controlled example CT and the third comparison example ED. As shown in FIG. 15, the cell numbers of NIH 3T3 cells stimulated by the third comparison example ED and the thermoelectric driving wearable system at the voltage value L3 are increased apparently, but the cell number of NIH 3T3 cells stimulated by thermoelectric driving wearable system at the voltage value L4 (5.0 V) is less than the cell number of the third controlled example CT (without any stimulation).

Fourth Treatment Example

Figure 16:
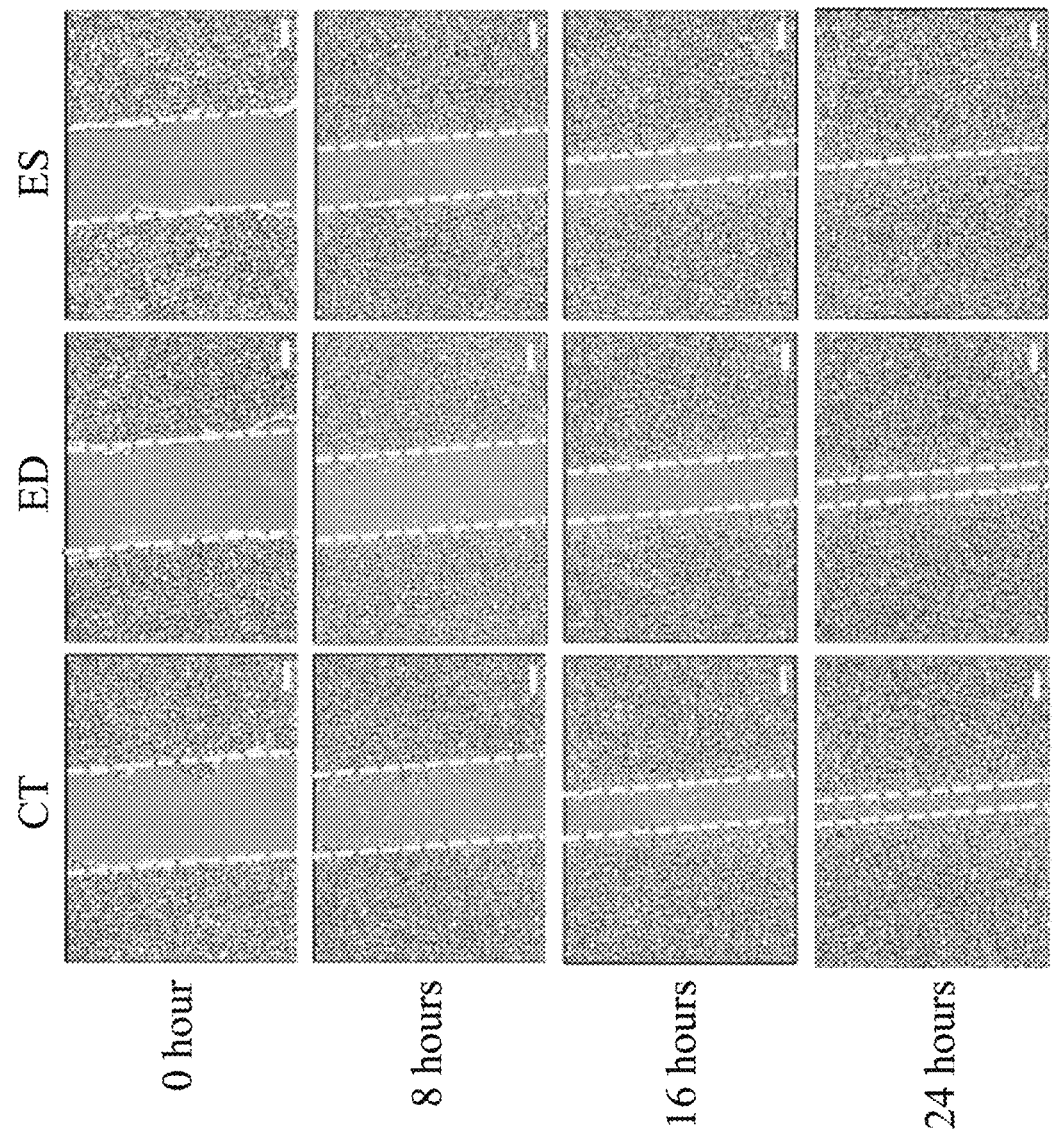
FIG. 16 shows a schematic view of cell migration of NIH 3T3 cells stimulated by the thermoelectric driving wearable system according to a fourth treatment example of the present disclosure, a fourth controlled example and a fourth comparison example in an electron microscope.

FIG. 16 shows a schematic view of cell migration of NIH 3T3 cells stimulated by the thermoelectric driving wearable system ES according to a fourth treatment example of the present disclosure, a fourth controlled example CT and a fourth comparison example ED in an electron microscope. As shown in FIG. 16, NIH 3T3 cells stimulated by the thermoelectric driving wearable system ES and the fourth comparison example ED are observed in the electron microscope. For stimulation from 0 hour to 24 hours, the change of cell migration between NIH 3T3 cells stimulated by the thermoelectric driving wearable system ES can reach to 20% after 24 hours (one day).

Fifth Treatment Example

Figure 17:
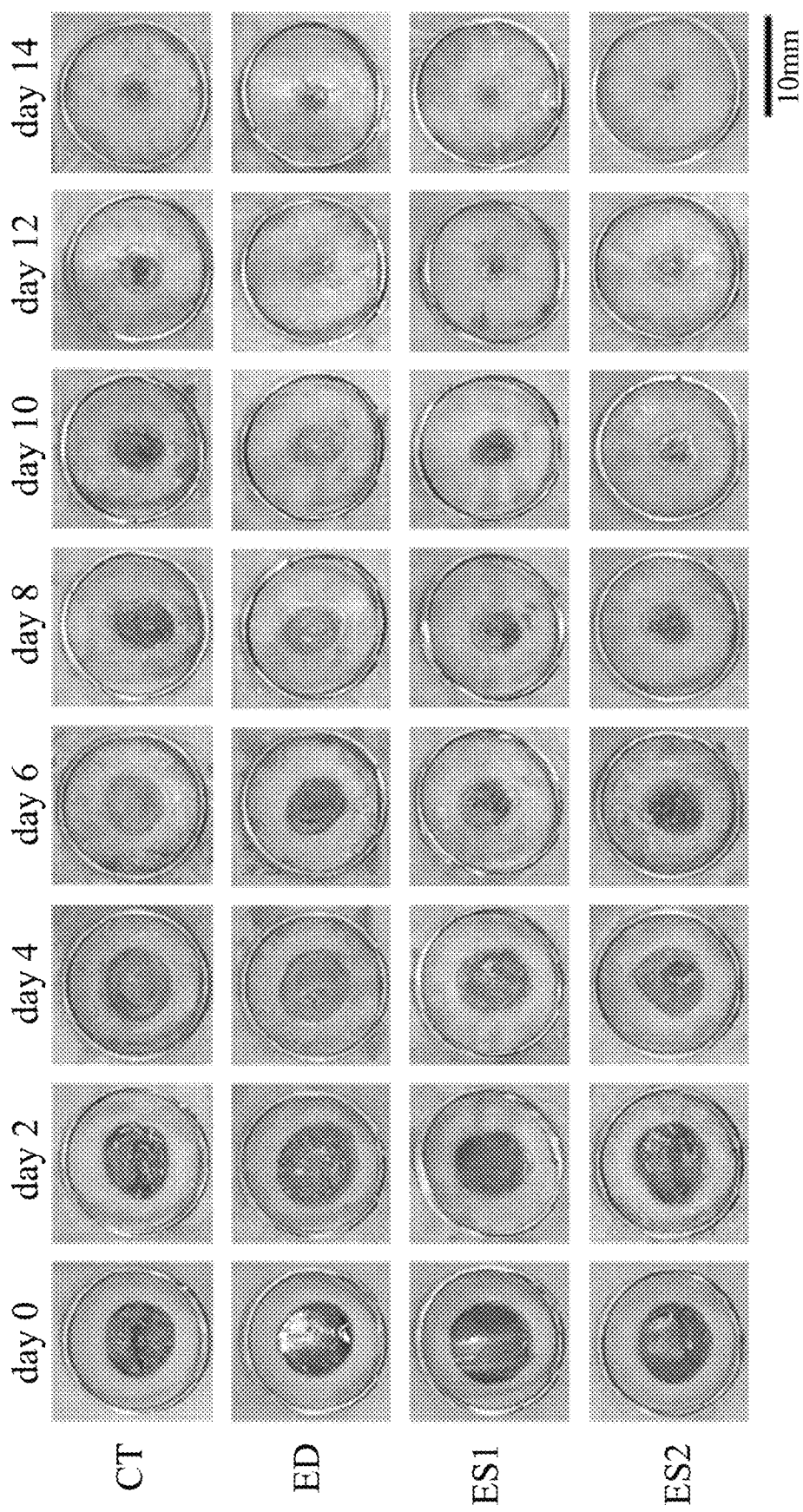
FIG. 17 shows pictures of a wound area stimulated by the thermoelectric driving wearable systems according to a fifth treatment example of the present disclosure, a fifth controlled example and a fifth comparison example.
Figure 18:
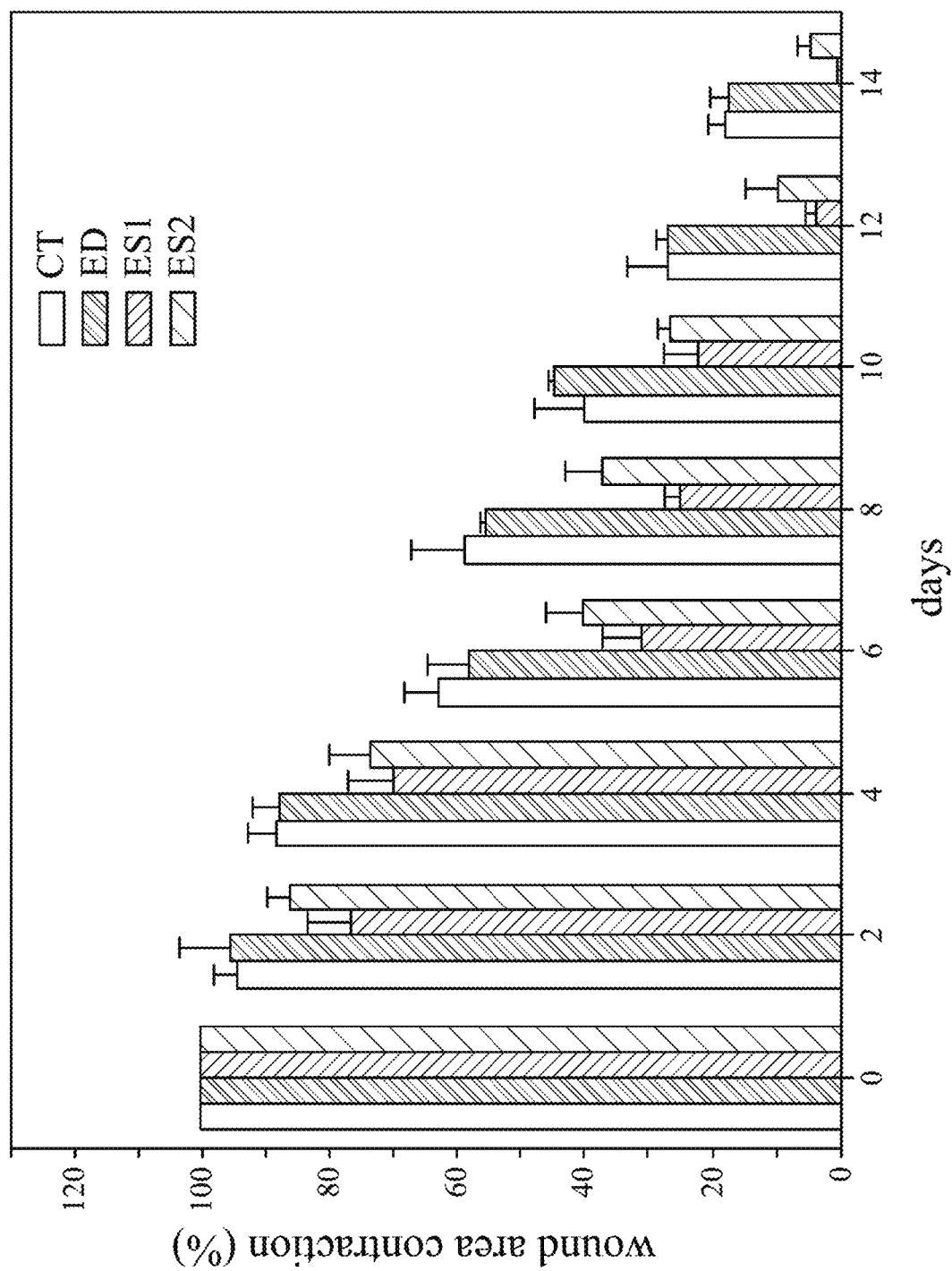
FIG. 18 shows a measurement of wound area contractions of the thermoelectric driving wearable system according to the fifth treatment example in FIG. 17, the fifth controlled example and the fifth comparison example.

FIG. 17 shows pictures of a wound area stimulated by the thermoelectric driving wearable systems ES1, ES2 according to a fifth treatment example of the present disclosure, a fifth controlled example CT and a fifth comparison example ED. FIG. 18 shows a measurement of wound area contractions of the thermoelectric driving wearable systems ES1, ES2 according to the fifth treatment example in FIG. 17, the fifth controlled example CT and the fifth comparison example ED. It is worthy to be mentioned that the thermoelectric driving wearable system ES1 provides the current to stimulate the wound area according to an electrically stimulating frequency, the electrically stimulating frequency of the thermoelectric driving wearable system ES1 is 35 s per day, and the electrically stimulating frequency of the thermoelectric driving wearable system ES2 is 5 min per day. As shown in FIGS. 17 and 18, curing rates of the wound area stimulated by the thermoelectric driving wearable systems ES1, ES2 are higher than the curing rates of the fifth controlled example CT and the fifth comparison example ED. Moreover, after 14 days, the wound area contraction of the wound area stimulated by the thermoelectric driving wearable system ES1 is close to 0%, which means that the wound area is recovered.

The thermoelectric driving wearable systems ES1, ES2 can detect a resistance value of the wound area by the monitoring module, estimate a recovery level of the wound area according to a ratio between the resistance value of the wound area and a resistance value of a normal skin, and transmit a monitoring signal to an electronic device. The resistance value of the normal skin is a resistance value of the skin surface of a mouse without injury. The thermoelectric driving wearable systems ES1, ES2 can estimate the recovery level of the wound area according to a recovery index, and the recovery index is a percentage ratio between the resistance value of the wound area and the resistance value of the normal skin. When the resistance value of the wound area equals to the resistance value of the normal skin, the recovery index is 100%, which means that the wound is recovered. Therefore, it is favorable for the user to judge the progress of recovery of the wound area.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A thermoelectric driving wearable system, comprising:
   a thermoelectric device, comprising:
      two thermal interface material layers configured for contacting a heat source and a cold source, respectively; and
      a thermoelectric converting layer located between the two thermal interface material layers and configured for generating an electric energy according to a temperature difference between the heat source and the cold source; and
   an electrical stimulating assembly electrically connected to the thermoelectric device and configured for being disposed at a skin surface, and the electrical stimulating assembly receiving the electric energy and transmitting a current to a stimulated region, the electrical stimulating assembly comprising:
      a cover membrane configured for covering the stimulated region;
      a first electrode assembly disposed on the cover membrane, electrically connected to a positive electrode and having a plurality of first comb electrodes, and the first comb electrodes configured for contacting the stimulated region; and
      a second electrode assembly disposed on the cover membrane, electrically connected to a negative electrode and having a plurality of second comb electrodes, and the second comb electrodes configured for contacting the stimulated region;
   wherein the first comb electrodes are electrically isolated from the second comb electrodes, the first comb electrodes and the second comb electrodes form a current stimulating region that is a round region, and each of the first comb electrodes and each of the second comb electrodes that is adjacent thereto form a plurality of concentric circular sections with different diameters.

2. The thermoelectric driving wearable system of claim 1, wherein the first electrode assembly and the second electrode assembly are made of gold, each of the first electrode assembly and the second electrode assembly is doped by a plurality of nanoparticles, and the nanoparticles are selected from iron (Fe), cupper (Cu), magnesium (Mg), manganese (Mn), calcium (Ca), potassium (K), aluminum (Al), selenium (Se), and a group composed of a combination thereof.

3. The thermoelectric driving wearable system of claim 2, wherein each of the nanoparticles is a selenium nanoparticle.

4. The thermoelectric driving wearable system of claim 1, wherein an electrode distance is included between each of the first comb electrodes and each of the second comb electrodes which is adjacent thereto, and the electrode distance is ranged between 1 mm-6 mm.

5. The thermoelectric driving wearable system of claim 1, wherein each of the two thermal interface material layers is made of an elastic material.

6. The thermoelectric driving wearable system of claim 5, wherein the elastic material is made of an aluminum nitride material or an elastic silicone composite material.

7. The thermoelectric driving wearable system of claim 1, wherein the thermoelectric device further comprises a plurality of upper electrodes, a plurality of first lower electrodes and a plurality of second lower electrodes, one of the two thermal interface material layers covers the upper electrodes, and the other one of the thermal interface material layers covers the first lower electrodes and the second lower electrodes.

8. The thermoelectric driving wearable system of claim 1, further comprising a pulse generating module electrically connected between the thermoelectric device and the electrical stimulating assembly, and the pulse generating module configured for turning on the electrical stimulating assembly intermittently according to a pulse duration, wherein the pulse duration is ranged between 50 ms-200 ms.

9. The thermoelectric driving wearable system of claim 1, further comprising a boosting and rectifying module electrically connected between the thermoelectric device and the electrical stimulating assembly, the boosting and rectifying module configured for converting the electric energy from an alternate current form to a direct current form, and modulating a voltage value of the electric energy.

10. The thermoelectric driving wearable system of claim 9, wherein the voltage value is ranged between 2 V to 5 V.

11. The thermoelectric driving wearable system of claim 1, further comprising a monitoring module electrically connected to the electrical stimulating assembly, the monitoring module configured for detecting a resistance value of the stimulated region and estimating a recovery level of the stimulated region according to a ratio between the resistance value of the stimulated region and a resistance value of a normal skin, and the monitoring module transmitting a monitoring signal to an electronic device.

12. The thermoelectric driving wearable system of claim 1, wherein the thermoelectric device further comprises a heat sink element disposed between the cold source and one of the two thermal interface material layers which contacts the cold source.

* * * * *